United States Patent
Braido et al.

(10) Patent No.: US 10,179,042 B2
(45) Date of Patent: Jan. 15, 2019

(54) HEART VALVE REPAIR AND REPLACEMENT

(71) Applicant: St. Jude Medical, Cardiology Division, Inc., St. Paul, MN (US)

(72) Inventors: Peter N. Braido, Wyoming, MN (US); Mina S. Fahim, Shoreview, MN (US); Thomas M. Benson, Minneapolis, MN (US); Theodore Paul Dale, Corcoran, MN (US); Andrea N. Para, Centennial, CO (US); Mark Krans, Hopkins, MN (US); Mathias Charles Glimsdale, St. Michael, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 15/177,598

(22) Filed: Jun. 9, 2016

(65) Prior Publication Data

US 2016/0361161 A1 Dec. 15, 2016

Related U.S. Application Data (60) Provisional application No. 62/174,690, filed on Jun. 12, 2015.

(51) Int. Cl.
*A61F 2/24* (2006.01)

(52) U.S. Cl.
CPC .......... *A61F 2/2418* (2013.01); *A61F 2/2409* (2013.01); *A61F 2/2469* (2013.01);
(Continued)

(58) Field of Classification Search
CPC .......... A61F 2/24; A61F 2/2412; A61F 2/2418
See application file for complete search history.

(56) References Cited

U.S. PATENT DOCUMENTS

| 3,657,744 A | 4/1972 | Ersek |
| 4,275,469 A | 6/1981 | Gabbay |
| (Continued) | | |

FOREIGN PATENT DOCUMENTS

| DE | 19857887 A1 | 7/2000 |
| DE | 10121210 A1 | 11/2002 |
| (Continued) | | |

OTHER PUBLICATIONS

"Closed heart surgery: Back to the future", Samuel V. Lichtenstein, The Journal of Thoracic and Cardiovascular Surgery, vol. 131, No. 5, pp. 941-943.
(Continued)

*Primary Examiner* — Alvin Stewart
(74) *Attorney, Agent, or Firm* — Lerner, David, Littenberg, Krumholz & Mentlik, LLP (57) ABSTRACT

A prosthetic heart valve having an inflow end and an outflow end includes a collapsible and expandable stent having a plurality of commissure features, a plurality of first struts and a plurality of second struts. The plurality of first struts define a substantially cylindrical portion and the plurality of second struts have first ends attached to the cylindrical portion and free ends projecting radially outward from the cylindrical portion and configured to couple to adjacent heart tissue to anchor the stent. A collapsible and expandable valve assembly disposed within the stent has a plurality of leaflets coupled to the commissure features.

5 Claims, 7 Drawing Sheets (52) U.S. Cl.
CPC ............... *A61F 2220/0008* (2013.01); *A61F 2220/0016* (2013.01); *A61F 2230/0006* (2013.01); *A61F 2230/0069* (2013.01)

(56) References Cited

U.S. PATENT DOCUMENTS

| | | | |
|---|---|---|---|
| 4,491,986 A | 1/1985 | Gabbay | |
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,415,664 A | 5/1995 | Pinchuk | |
| 5,480,423 A | 1/1996 | Ravenscroft et al. | |
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,458,153 B1 | 10/2002 | Bailey et al. | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,374,573 B2 | 5/2008 | Gabbay | |
| 7,381,218 B2 | 6/2008 | Schreck | |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,914,569 B2 | 3/2011 | Nguyen et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| 8,591,570 B2 * | 11/2013 | Revuelta | A61F 2/2418 623/1.26 |
| 8,840,663 B2 | 9/2014 | Salahieh et al. | |
| 9,289,291 B2 * | 3/2016 | Gorman, III | A61F 2/2418 |
| 9,480,556 B2 * | 11/2016 | Revuelta | A61F 2/2418 |
| 9,629,721 B2 * | 4/2017 | McKinnis | A61F 2/2475 |
| 9,763,778 B2 * | 9/2017 | Eidenschink | A61F 2/2409 |
| 2002/0036220 A1 | 3/2002 | Gabbay | |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0210304 A1 | 10/2004 | Seguin et al. | |
| 2005/0096726 A1 | 5/2005 | Sequin et al. | |
| 2005/0137690 A1 * | 6/2005 | Salahieh | A61F 2/2418 623/2.11 |
| 2005/0137695 A1 | 6/2005 | Salahieh et al. | |
| 2005/0137697 A1 | 6/2005 | Salahieh et al. | |
| 2005/0240200 A1 | 10/2005 | Bergheim | |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0173532 A1 | 8/2006 | Flagle et al. | |
| 2006/0178740 A1 * | 8/2006 | Stacchino | A61F 2/2418 623/2.18 |
| 2006/0190074 A1 * | 8/2006 | Hill | A61F 2/2412 623/1.23 |
| 2006/0195180 A1 | 8/2006 | Kheradvar et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259136 A1 * | 11/2006 | Nguyen | A61F 2/2412 623/2.18 |
| 2006/0259137 A1 | 11/2006 | Artof et al. | |
| 2006/0265056 A1 | 11/2006 | Nguyen et al. | |
| 2006/0271166 A1 * | 11/2006 | Thill | A61F 2/2418 623/1.23 |
| 2006/0276813 A1 | 12/2006 | Greenberg | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071361 A1 * | 3/2008 | Tuval | A61F 2/2418 623/2.1 |
| 2008/0071362 A1 * | 3/2008 | Tuval | A61F 2/2418 623/2.1 |
| 2008/0071366 A1 * | 3/2008 | Tuval | A61F 2/2418 623/2.11 |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255660 A1 * | 10/2008 | Guyenot | A61F 2/2418 623/2.14 |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |

(56) References Cited

U.S. PATENT DOCUMENTS

| | | | |
|---|---|---|---|
| 2009/0054976 A1* | 2/2009 | Tuval | A61F 2/0095 623/2.11 |
| 2009/0112309 A1 | 4/2009 | Jaramillo et al. | |
| 2009/0138079 A1 | 5/2009 | Tuval et al. | |
| 2009/0157175 A1* | 6/2009 | Benichou | A61F 2/2412 623/2.18 |
| 2009/0287299 A1* | 11/2009 | Tabor | A61F 2/013 623/1.26 |
| 2010/0004740 A1 | 1/2010 | Seguin et al. | |
| 2010/0036484 A1 | 2/2010 | Hariton et al. | |
| 2010/0049306 A1 | 2/2010 | House et al. | |
| 2010/0082094 A1* | 4/2010 | Quadri | A61F 2/2412 623/1.26 |
| 2010/0087907 A1 | 4/2010 | Lattouf | |
| 2010/0131055 A1 | 5/2010 | Case et al. | |
| 2010/0168778 A1 | 7/2010 | Braido | |
| 2010/0168839 A1 | 7/2010 | Braido et al. | |
| 2010/0185277 A1 | 7/2010 | Braido et al. | |
| 2010/0191326 A1 | 7/2010 | Alkhatib | |
| 2010/0204781 A1* | 8/2010 | Alkhatib | A61F 2/2418 623/1.26 |
| 2010/0204785 A1 | 8/2010 | Alkhatib | |
| 2010/0217382 A1 | 8/2010 | Chau et al. | |
| 2010/0249911 A1 | 9/2010 | Alkhatib | |
| 2010/0249923 A1* | 9/2010 | Alkhatib | A61F 2/2418 623/2.18 |
| 2010/0256723 A1 | 10/2010 | Murray | |
| 2010/0286768 A1 | 11/2010 | Alkhatib | |
| 2010/0298931 A1* | 11/2010 | Quadri | A61F 2/2418 623/2.11 |
| 2011/0029072 A1 | 2/2011 | Gabbay | |
| 2011/0098802 A1* | 4/2011 | Braido | A61F 2/2412 623/1.26 |
| 2011/0137397 A1* | 6/2011 | Chau | A61F 2/2418 623/1.11 |
| 2011/0218620 A1* | 9/2011 | Meiri | A61B 17/0487 623/2.11 |
| 2011/0238168 A1* | 9/2011 | Pellegrini | A61F 2/2412 623/2.17 |
| 2011/0264206 A1* | 10/2011 | Tabor | A61F 2/2418 623/2.12 |
| 2011/0313515 A1 | 12/2011 | Quadri et al. | |
| 2012/0035722 A1* | 2/2012 | Tuval | A61F 2/2418 623/2.37 |
| 2012/0078347 A1* | 3/2012 | Braido | A61F 2/2418 623/1.26 |
| 2012/0215303 A1* | 8/2012 | Quadri | A61F 2/2418 623/2.18 |
| 2012/0303116 A1* | 11/2012 | Gorman, III | A61F 2/2418 623/2.11 |
| 2013/0150956 A1* | 6/2013 | Yohanan | A61F 2/2418 623/2.14 |
| 2013/0184813 A1* | 7/2013 | Quadri | A61F 2/2412 623/2.18 |
| 2013/0211508 A1* | 8/2013 | Lane | A61F 2/2403 623/2.11 |
| 2013/0274870 A1* | 10/2013 | Lombardi | A61F 2/2418 623/2.11 |
| 2013/0274873 A1* | 10/2013 | Delaloye | A61F 2/2409 623/2.18 |
| 2014/0005771 A1* | 1/2014 | Braido | A61F 2/2412 623/2.12 |
| 2014/0018911 A1* | 1/2014 | Zhou | A61F 2/2436 623/2.11 |
| 2014/0018915 A1* | 1/2014 | Biadillah | A61F 2/2418 623/2.17 |
| 2014/0046433 A1* | 2/2014 | Kovalsky | A61F 2/2418 623/1.26 |
| 2014/0228940 A1* | 8/2014 | McKinnis | A61F 2/2475 623/1.24 |
| 2014/0236292 A1 | 8/2014 | Braido | |
| 2014/0243965 A1* | 8/2014 | Benson | A61F 2/2418 623/2.18 |
| 2014/0249621 A1 | 9/2014 | Eidenschink | |
| 2014/0277425 A1* | 9/2014 | Dakin | A61B 17/12122 623/2.38 |
| 2014/0324164 A1* | 10/2014 | Gross | A61F 2/2409 623/2.37 |
| 2014/0330371 A1* | 11/2014 | Gloss | A61F 2/2418 623/2.17 |
| 2015/0351904 A1* | 12/2015 | Cooper | A61F 2/2418 623/2.1 |
| 2016/0030165 A1* | 2/2016 | Mitra | A61F 2/2409 623/2.42 |
| 2016/0030171 A1* | 2/2016 | Quijano | A61F 2/243 623/1.12 |
| 2016/0067038 A1* | 3/2016 | Park | A61F 2/2406 623/2.18 |
| 2016/0074160 A1* | 3/2016 | Christianson | A61F 2/24 623/2.18 |
| 2016/0081799 A1* | 3/2016 | Leo | A61F 2/2418 623/1.18 |
| 2016/0095701 A1* | 4/2016 | Dale | A61F 2/2412 623/2.18 |
| 2016/0113768 A1* | 4/2016 | Ganesan | A61F 2/2403 623/2.17 |
| 2016/0158003 A1* | 6/2016 | Wallace | A61F 2/2409 623/2.17 |
| 2016/0158007 A1* | 6/2016 | Centola | A61F 2/2439 623/1.26 |
| 2016/0199180 A1* | 7/2016 | Zeng | A61F 2/2418 623/2.17 |
| 2016/0228249 A1* | 8/2016 | Mantanus | A61F 2/2436 |
| 2016/0235529 A1* | 8/2016 | Ma | A61F 2/2418 |
| 2016/0278922 A1* | 9/2016 | Braido | A61F 2/2409 |
| 2016/0278923 A1* | 9/2016 | Krans | A61F 2/2409 |
| 2016/0302918 A1* | 10/2016 | Keidar | A61F 2/2409 |
| 2016/0302919 A1* | 10/2016 | Scorsin | A61F 2/2412 |
| 2016/0310268 A1* | 10/2016 | Oba | A61F 2/2418 |
| 2016/0317301 A1* | 11/2016 | Quadri | A61F 2/2436 |
| 2016/0331525 A1* | 11/2016 | Straubinger | A61F 2/07 |
| 2016/0361161 A1* | 12/2016 | Braido | A61F 2/2418 |
| 2017/0000604 A1* | 1/2017 | Conklin | A61F 2/2418 |
| 2017/0042673 A1* | 2/2017 | Vietmeier | A61F 2/2418 |
| 2017/0049565 A1* | 2/2017 | Bailey | A61F 2/2418 |
| 2017/0056169 A1* | 3/2017 | Johnson | A61F 2/2418 |
| 2017/0071733 A1* | 3/2017 | Ghione | A61F 2/2412 |
| 2017/0079786 A1* | 3/2017 | Li | A61F 2/2418 |
| 2017/0095326 A1* | 4/2017 | Lim | A61F 2/2418 |
| 2017/0095328 A1* | 4/2017 | Cooper | A61F 2/2418 |
| 2017/0112621 A1* | 4/2017 | Salahieh | A61F 2/2418 |
| 2017/0128204 A1* | 5/2017 | Morriss | A61F 2/2418 |
| 2017/0128207 A1* | 5/2017 | Tuval | A61F 2/2436 |
| 2017/0143481 A1* | 5/2017 | Morriss | A61F 2/2418 |
| 2017/0143482 A1* | 5/2017 | Kveen | A61F 2/2418 |
| 2017/0143484 A1* | 5/2017 | Braido | A61F 2/2418 |
| 2017/0143485 A1* | 5/2017 | Gorman, III | A61F 2/2418 |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1926455 A2 | 6/2008 |
| EP | 2777616 A1 | 9/2014 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01/028459 A1 | 4/2001 |
| WO | 0149213 A2 | 7/2001 |
| WO | 01054625 A1 | 8/2001 |

(56) References Cited

FOREIGN PATENT DOCUMENTS

| WO | 01056500 A2 | 8/2001 |
|---|---|---|
| WO | 01076510 A2 | 10/2001 |
| WO | 0236048 A1 | 5/2002 |
| WO | 0247575 A2 | 6/2002 |
| WO | 02067782 A2 | 9/2002 |
| WO | 03047468 A1 | 6/2003 |
| WO | 2005070343 A1 | 8/2005 |
| WO | 06073626 A2 | 7/2006 |
| WO | 07071436 A2 | 6/2007 |
| WO | 08070797 A2 | 6/2008 |
| WO | 10008549 A1 | 1/2010 |
| WO | 2010008548 A2 | 1/2010 |
| WO | 10096176 A1 | 8/2010 |
| WO | 10098857 A1 | 9/2010 |
| WO | 2012068377 A1 | 5/2012 |

OTHER PUBLICATIONS

"Direct-Access Valve Replacement", Christoph H. Huber, et al., Journal of the American College of Cardiology, vol. 46, No. 2, (Jul. 19, 2005).

"Minimally invasive cardiac surgery", M. J. Mack, Surgical Endoscopy, 2006, 20:S488-S492, DOI: 10.1007/s00464-006-0110-8 (presented Apr. 24, 2006).

"Percutaneous Aortic Valve Implantation Retrograde From the Femoral Artery", John G. Webb et al., Circulation, 2006; 113:842-850 (Feb. 6, 2006).

"Transapical aortic valve implantation: an animal feasibility study"; Todd M. Dewey et al., The annals of thoracic surgery 2006; 82: 110-6 (Feb. 13, 2006).

"Transapical approach for sutureless stent-fixed aortic valve implantation: experimental results"; Th. Walther et al., European Journal of Cardio-thoracic Surgery 29 (2006) 703-708 (Jan. 30, 2006).

"Transapical Transcatheter Aortic Valve Implantation in Humans", Samuel V. Lichtenstein et al., Circulation. 2006; 114: 591-596 (Jul. 31, 2006).

Catheter-implanted prosthetic heart valves, Knudsen, L.L., et al., The International Journal of Artificial Organs, vol. 16, No. 5 1993, pp. 253-262.

International Search Report for Application No. PCT/US2016/036560 dated Aug. 18, 2016.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

Percutaneous aortic valve replacement: resection before implantation, 836-840, Quaden, Rene et al., European J. of Cardio-thoracic Surgery, 27 (2005).

Textbook "Transcatheter Valve Repair", 2006, pp. 165-186.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

U.S. Appl. No. 29/375,243, filed Sep. 20, 2010.

U.S. Appl. No. 29/375,260, filed Sep. 20, 2010.

\* cited by examiner

FIG. 1

*(PRIOR ART)*

HEART VALVE REPAIR AND REPLACEMENT

CROSS-REFERENCE TO RELATED APPLICATIONS

The present application claims the benefit of the filing date of U.S. Provisional Patent Application No. 62/174,690 filed Jun. 12, 2015, the disclosure of which is hereby incorporated herein by reference.

BACKGROUND OF THE INVENTION

The present disclosure relates to heart valve repair and, in particular, to collapsible prosthetic heart valves. More particularly, the present disclosure relates to devices and methods for repairing and/or replacing the functionality of native valve leaflets.

Diseased and/or defective heart valves may lead to serious health complications. One method of addressing this condition is to replace a non-functioning heart valve with a prosthetic valve. Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

SUMMARY OF THE INVENTION

In some embodiments, a prosthetic heart valve having an inflow end and an outflow end, includes a collapsible and expandable stent having a plurality of commissure features, a plurality of first struts and a plurality of second struts. The plurality of first struts define a substantially cylindrical portion of the stent and the plurality of second struts have first ends attached to the cylindrical portion and free ends projecting radially outward of the cylindrical portion and configured to couple to adjacent heart tissue to anchor the stent. A collapsible and expandable valve assembly is disposed within the stent and has a plurality of leaflets coupled to the commissure features.

BRIEF DESCRIPTION OF THE DRAWINGS

Various embodiments of the present disclosure are disclosed herein with reference to the drawings, wherein.

Various embodiments of the present disclosure will now be described with reference to the appended drawings. It is to be appreciated that these drawings depict only some embodiments of the disclosure and are therefore not to be considered limiting of its scope.

DETAILED DESCRIPTION

In conventional collapsible prosthetic heart valves, the stent is usually anchored within the native valve annulus via radial forces exerted by the expanding stent against the native valve annulus. If the radial force is too high, damage may occur to heart tissue. If, instead, the radial force is too low, the heart valve may move from its implanted position, for example, into the left ventricle. Because such anchoring partly depends on the presence of calcification or plaque in the native valve annulus, it may be difficult to properly anchor the valve in locations where plaque is lacking (e.g., the mitral valve annulus).

In view of the foregoing, there is a need for further improvements to the devices, systems, and methods for restoring and/or replacing the function of a native heart valve, such as a mitral valve, a tricuspid valve, an aortic valve, or a pulmonary valve. Among other advantages, the present disclosure may address one or more of these needs. While many of the examples disclosed herein are described with reference to a specific valve (e.g., a mitral valve or a tricuspid valve), it will be understood that many of the examples are not so limited and that the concepts described apply equally to other heart valves unless expressly limited herein.

Blood flows through the mitral valve from the left atrium to the left ventricle. As used herein, the term "inflow," when used in connection with a prosthetic mitral heart valve, refers to the end of the heart valve closest to the left atrium when the heart valve is implanted in a patient, whereas the term "outflow," when used in connection with a prosthetic mitral heart valve, refers to the end of the heart valve closest to the left ventricle when the heart valve is implanted in a patient. When used in connection with a prosthetic aortic valve, "inflow" refers to the end closest to the left ventricle and "outflow" refers to the end closest to the aorta. The same convention is applicable for other valves wherein "inflow" and "outflow" are defined by the direction of blood flow therethrough. "Trailing" is to be understood as relatively close to the user, and "leading" is to be understood as relatively farther away from the user. As used herein, the terms "proximal," "distal," "leading" and "trailing" are to be taken as relative to a user using the disclosed delivery devices. "Proximal" or "trailing end" are to be understood as relatively close to the user and "distal" or "leading end" are to be understood as relatively farther away from the user. Also, as used herein, the words "substantially," "approximately," "generally" and "about" are intended to mean that slight variations from absolute are included within the scope of the structure or process recited.

Figure 1:
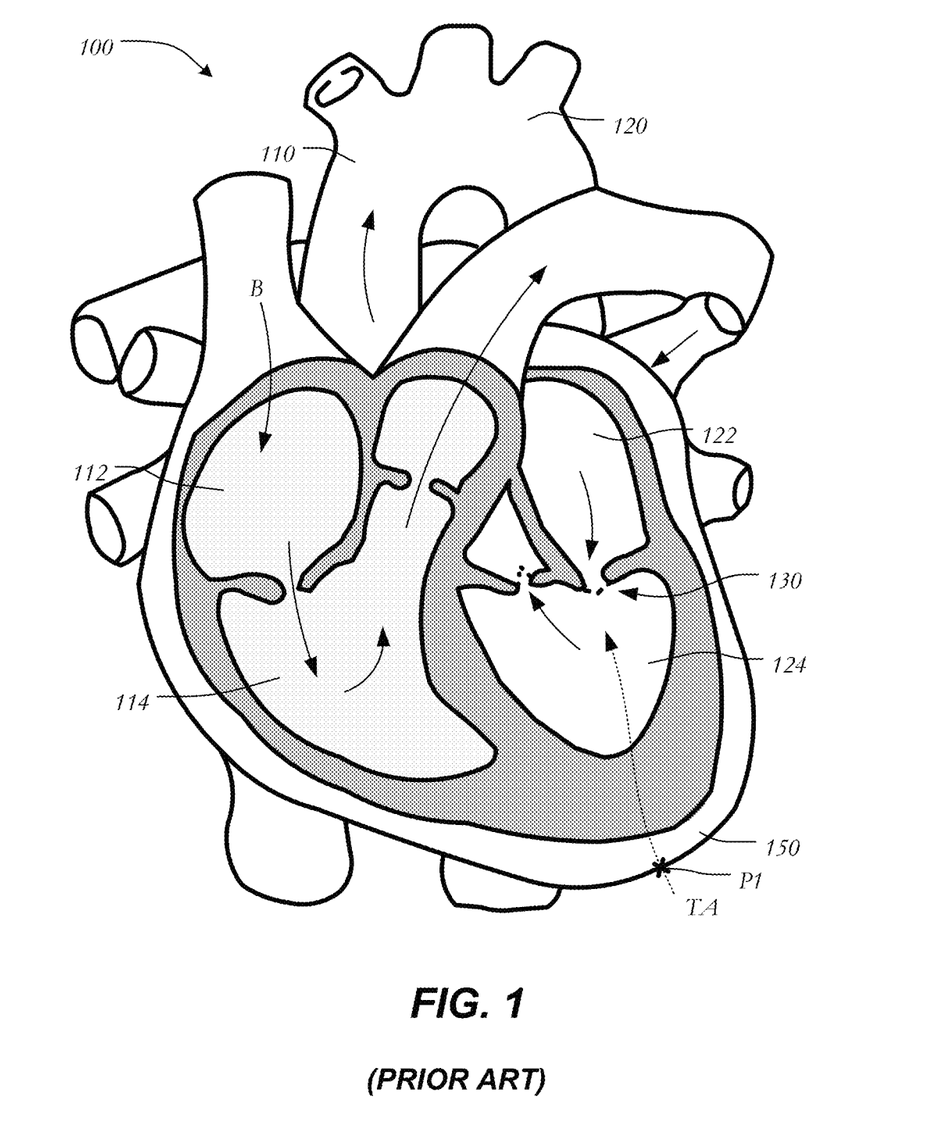
FIG. 1 is a schematic cutaway representation of a human heart showing a transapical delivery approach.

FIG. 1 is a schematic representation of a human heart 100. The human heart includes two atria and two ventricles: a right atrium 112 and a left atrium 122, and a right ventricle 114 and a left ventricle 124. As illustrated in FIG. 1, the heart 100 further includes an aorta 110, and an aortic arch 120. Disposed between the left atrium and the left ventricle is the mitral valve 130. The mitral valve 130, also known as the bicuspid valve or left atrioventricular valve, is a dual-flap that opens as a result of increased pressure in the left atrium as it fills with blood. As atrial pressure increases above that of the left ventricle, the mitral valve opens and blood passes toward the left ventricle. Blood flows through heart 100 in the direction shown by arrows "B".

A dashed arrow, labeled "TA", indicates a transapical approach for repairing or replacing heart valves, such as a mitral valve. In transapical delivery, a small incision is made between the ribs and into the apex of the left ventricle 124 at position "P1" in heart wall 150 to deliver a prosthesis or device to the target site.

Figures 2A, 2B:
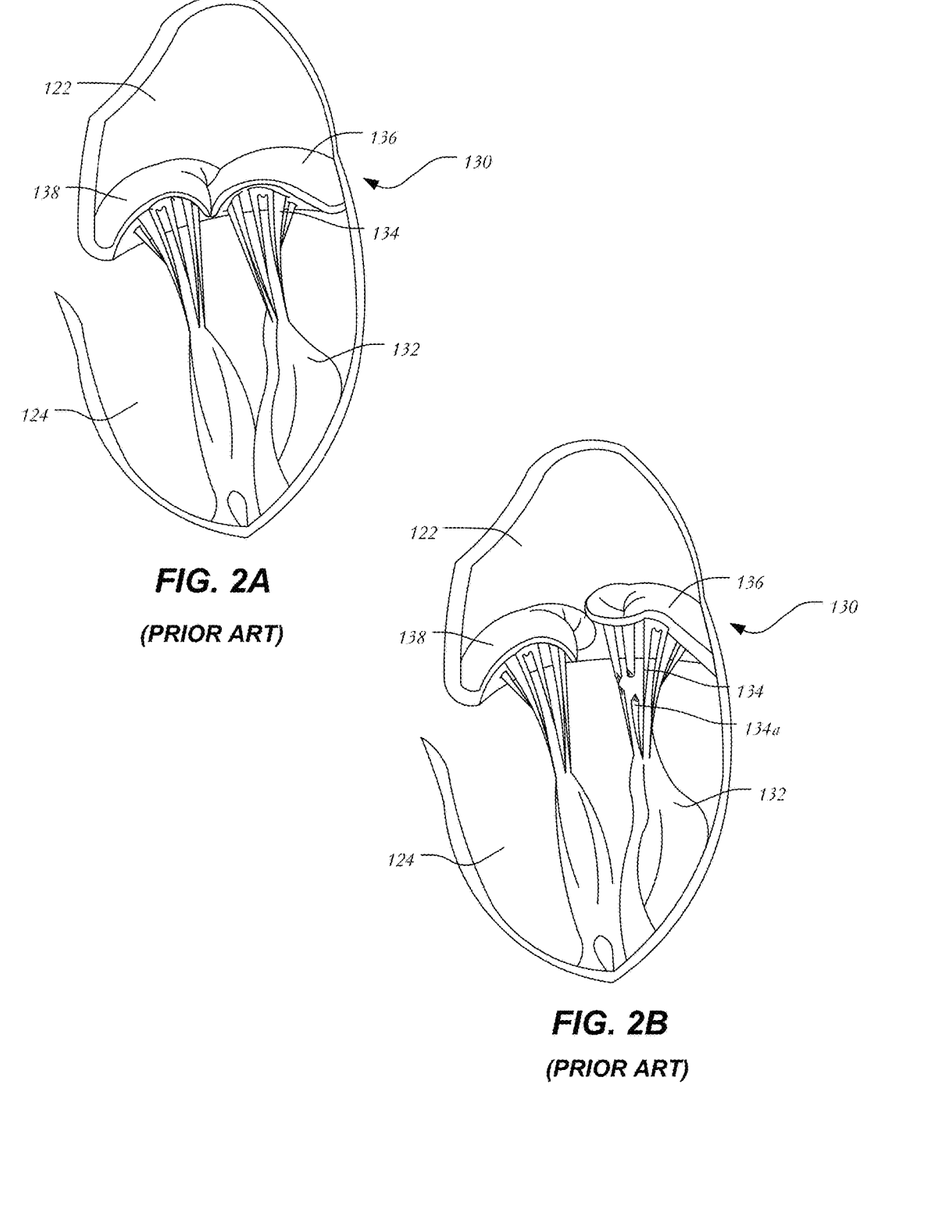
FIG. 2A is a schematic representation of a native mitral valve and associated structures during normal operation.
FIG. 2B is a schematic representation of a native mitral valve having a prolapsed leaflet.

FIG. 2A is a more detailed schematic representation of a native mitral valve 130 and its associated structures. Mitral valve 130 includes two flaps or leaflets, a posterior leaflet 136 and an anterior leaflet 138, disposed between left atrium 122 and left ventricle 124. Cord-like tendons known as chordae tendineae 134 connect the two leaflets 136, 138 to the medial and lateral papillary muscles 132. During atrial systole, blood flows from the left atrium to the left ventricle down the pressure gradient. When the left ventricle contracts in ventricular systole, the increased blood pressure in the chamber pushes the mitral valve to close, preventing backflow of blood into the left atrium. Since the blood pressure in the left atrium is much lower than that in the left ventricle, the flaps attempt to evert to the low pressure regions. The chordae tendineae prevent the eversion by becoming tense, thus pulling the flaps and holding them in the closed position.

FIG. 2B is a schematic representation of mitral valve prolapse as discussed above. Posterior leaflet 136 has prolapsed into left atrium 122. Moreover, certain chordae tendineae have stretched and others have ruptured. Because of damaged chordae 134a, even if posterior leaflet 136 returns to its intended position, it will eventually resume the prolapsed position due to being inadequately secured. Thus, mitral valve 130 is incapable of functioning properly and blood is allowed to return to the left atrium and the lungs. It will be understood that in addition to chordae damage, other abnormalities or failures may be responsible for mitral valve insufficiency.

Figure 3:
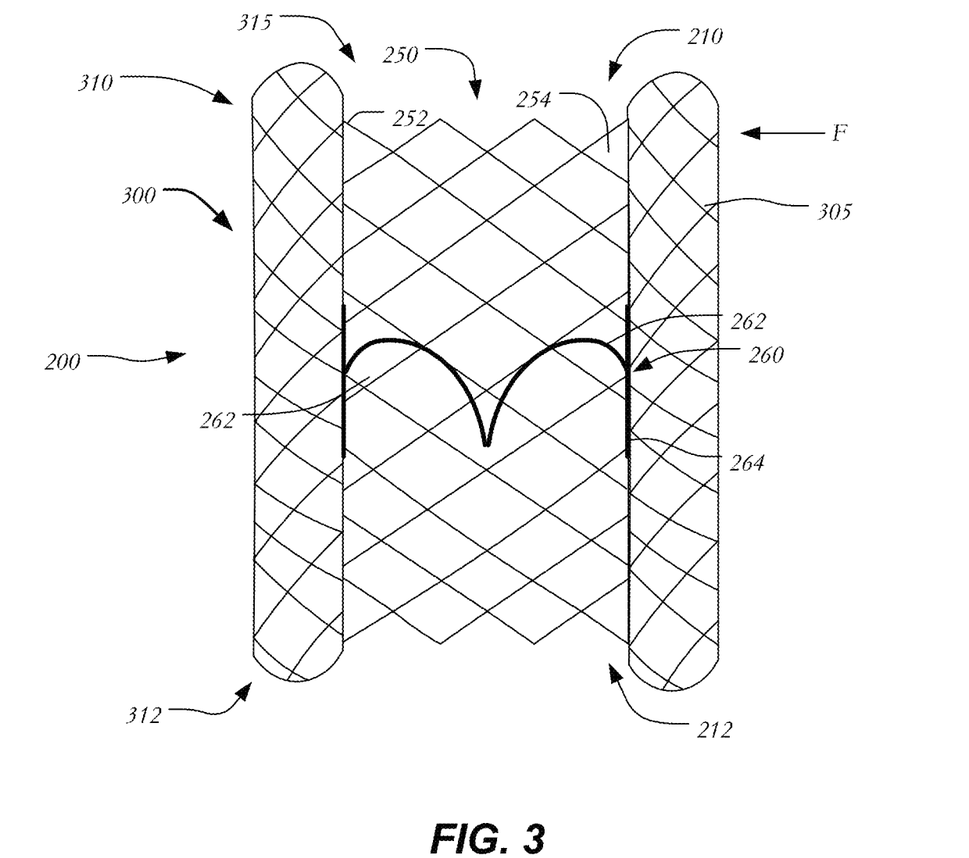
FIG. 3 is a schematic longitudinal cross-section of one embodiment of a prosthetic heart valve having a stent, a valve assembly, and a frame.

FIG. 3 is a longitudinal cross-section of prosthetic heart valve 200 in accordance with one embodiment of the present disclosure. Prosthetic heart valve 200 is a collapsible prosthetic heart valve designed to replace the function of the native mitral valve of a patient. (See native mitral valve 130 of FIGS. 1-2.) Generally, prosthetic valve 200 has inflow end 210 and outflow end 212. Prosthetic valve 200 may be substantially cylindrically shaped and may include features for anchoring, as will be discussed in more detail below. When used to replace native mitral valve 130, prosthetic valve 200 may have a low profile so as not to interfere with atrial function.

Prosthetic heart valve 200 includes stent 250, which may be formed from biocompatible materials that are capable of self-expansion, such as, for example, shape-memory alloys including nitinol. Alternatively, stent 250 may be formed of a material suitable for forming a balloon-expandable stent. Stent 250 may include a plurality of struts 252 that form closed cells 254 connected to one another in one or more annular rows around the stent. Cells 254 may all be of substantially the same size around the perimeter and along the length of stent 250. Alternatively, cells 254 near inflow end 210 may be larger than the cells near outflow end 212. Stent 250 may be expandable to provide a radial force to assist with positioning and stabilizing prosthetic heart valve 200 within the native mitral valve annulus.

Prosthetic heart valve 200 may also include valve assembly 260, including a pair of leaflets 262 attached to a cylindrical cuff 264. Leaflets 262 replace the function of native mitral valve leaflets 136 and 138 described above with reference to FIG. 2. That is, leaflets 262 coapt with one another to function as a one-way valve. It will be appreciated, however, that prosthetic heart valve 200 may have more than two leaflets when used to replace a mitral valve or other cardiac valves within a patient. Valve assembly 260 of prosthetic heart valve 200 may be substantially cylindrical, or may taper outwardly from outflow end 212 to inflow end 210. Both cuff 264 and leaflets 262 may be wholly or partly formed of any suitable biological material, such as bovine or porcine pericardium, or polymers, such as PTFE, urethanes and the like.

When used to replace a native mitral valve, valve assembly 260 may be sized in the range of about 20 mm to about 40 mm in diameter. Valve assembly 260 may be secured to stent 250 by suturing to struts 252 or by using tissue glue, ultrasonic welding or other suitable methods.

An optional frame 300 may surround and house valve assembly 260 and stent 250. Frame 300 may be formed of a braided material in various configurations to create shapes and/or geometries for engaging tissue and filling the spaces between valve assembly 260 and the native valve annulus. As shown in FIG. 3, frame 300 includes a plurality of braided strands or wires 305 arranged in three-dimensional shapes. In one example, wires 305 form a braided metal fabric that is both resilient and capable of heat treatment to substantially set a desired preset shape. One class of materials which meets these qualifications is shape-memory alloys. One example of a suitable shape-memory alloy is nitinol. It is also contemplated that wires 305 may comprise various materials other than nitinol that have elastic and/or memory properties, such as spring stainless steel, alloys such as Elgiloy®, Hastelloy®, and MP35N®, CoCrNi alloys (e.g., trade name Phynox), CoCrMo alloys, or a mixture of metal and polymer fibers. Depending on the individual material selected, the strand diameter, number of strands, and pitch may be altered to achieve desired properties for frame 300.

In its simplest configuration, shown in FIG. 3, frame 300 may be formed in a cylindrical or tubular configuration having inlet end 310, outlet end 312 and lumen 315 extending between inlet end 310 and outlet end 312 for housing stent 250 and valve assembly 260. However, in certain embodiments stent 250 may be omitted, and valve assembly 260 may be directly attached to frame 300 using any of the techniques described above for attaching valve assembly 260 to stent 250. Frame 300 may be radially collapsed from a relaxed or preset configuration to a compressed or reduced configuration for delivery into the patient. Once released after delivery, the shape-memory properties of frame 300 may cause it to re-expand to its relaxed or preset configuration. Frame 300 may also be locally compliant in a radial direction such that a force exerted in the direction of arrow F deforms a portion of the frame. In this manner, irregularities in the native valve annulus may be filled by frame 300, thereby preventing paravalvular leakage. Moreover, portions of frame 300 may endothelialize and in-grow into the heart wall over time, providing permanent stability and a low thrombus surface.

Figure 4:
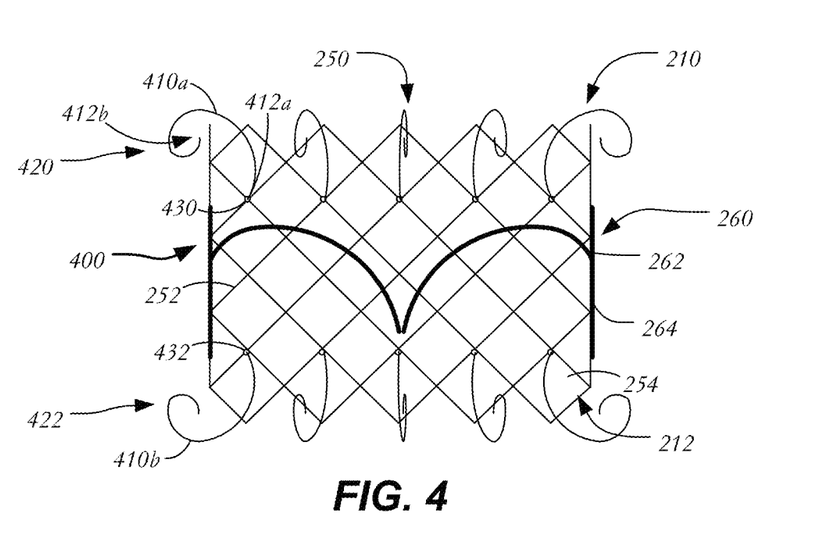
FIG. 4 is a schematic longitudinal cross-section of one embodiment of a prosthetic heart valve having a stent, a valve assembly, and curling struts.

FIG. 4 illustrates a variation in which prosthetic heart valve 400 includes outwardly curling struts to aid in its fixation to heart tissue. Prosthetic heart valve 400 may extend between inflow end 210 and outflow end 212 and include all the elements disclosed above including stent 250 formed of struts 252 defining cells 254, and valve assembly 260 having leaflets 262 and cuff 264. Stent 250 may be substantially cylindrical as shown and may further include two rows of curling struts 410a, 410b that project radially outward from the general stent body to anchor the stent at a predetermined location in the native valve annulus. A first row 420 of curling struts 410a is disposed adjacent inflow end 210 of prosthetic heart valve 400 and a second row 422 of curling struts 410b is disposed adjacent outflow end 212. Each curling strut 410a, 410b has a first end 412a connected to stent 250 and a free end 412b, with a curled configuration between these ends. Curling struts 410a, 410b may be formed of the same material as struts 252 and may be formed integrally with stent 250 by laser cutting from the same tube that forms stent 250 or separately formed and attached to stent 250 using welding techniques or other suitable methods. As shown in FIG. 4, the first end 412a of each curling strut 410a is connected to stent 250 at fixation points 430 at the bottom of the first full row of cells 254 adjacent inflow end 210 of prosthetic heart valve 400 and the first end 412a of each curling strut 410b is connected to stent 250 at fixation points 432 at the top of the last (i.e., bottom-most) full row of cells 254 adjacent outflow end 212 of the prosthetic heart valve. It will be understood that other fixation points (e.g., closer to inflow end 210 or further from inflow end 210) are possible.

As noted above, each curling strut 410a, 410b has a curled configuration between its ends. Curling struts 410a initially extend upward from fixation points 430 toward inflow end 210 before bending outwardly and downwardly toward outflow end 212 to form a substantially "fiddlehead" shape. Likewise, each curling strut 410b initially extends downward from a fixation point 432 toward outflow end 212 before bending outwardly and upwardly toward inflow end 210. Curling struts 410a, 410b may be subjected to heat treatment to substantially preset their desired curled shape. During the delivery of prosthetic heart valve 400 into a patient, curling struts 410a, 410b may be distorted to a substantially linear configuration within the sheath of a delivery device and may return to their curled configuration when released from the sheath.

When heart valve 400 is implanted, first row 420 of curling struts 410a may engage upper portions of the native mitral valve (i.e., portions of the native mitral valve in left atrium 122) or the atrial wall itself, while second row 422 of curling struts 410b may engage lower portions of the native mitral valve (i.e., portions of the native mitral valve in left ventricle 124) or the ventricular wall itself. The engagement of curling struts 410a and 410b with the surrounding native tissue may help to affix heart valve 400 in the proper position in the native mitral valve annulus.

Figure 5:
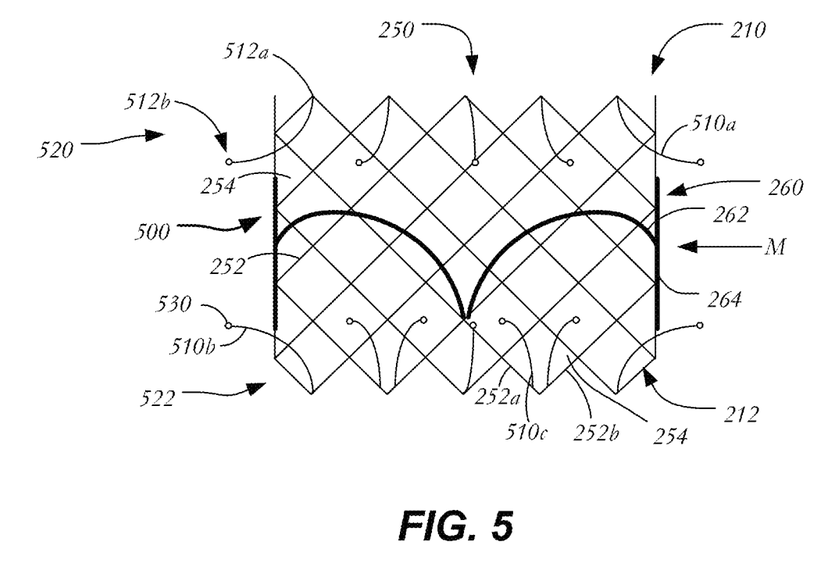
FIG. 5 is a schematic longitudinal cross-section of one embodiment of a prosthetic heart valve having a stent, a valve assembly, and curved struts.

FIG. 5 illustrates another variation in which prosthetic heart valve 500 includes projecting curved struts to aid in its fixation to heart tissue. Prosthetic heart valve 500 may extend between inflow end 210 and outflow end 212 and include all the elements described above in connection with heart valve 400, including stent 250 formed of struts 252 defining cells 254, and valve assembly 260 having leaflets 262 and cuff 264. As shown, prosthetic heart valve 500 includes two rows of curved struts 510a, 510b.

A first row 520 of curved struts 510a is disposed adjacent inflow end 210 of prosthetic heart valve 500 and a second row 522 of curved struts 510b is disposed adjacent outflow end 212. Each curved strut 510a, 510b has a first end 512a connected to stent 250, a free end 512b and a bowed configuration between these ends. Curved struts 510a, 510b may be formed of the same material as struts 252 and may be formed integrally with stent 250 by laser cutting from the same tube that forms stent 250 or separately and attached to stent 250 using welding or another suitable method. Curved struts 510a, 510b may be between about 3.0 mm and about 8.0 mm in length. In at least some examples, curved struts 510a, 510b are approximately 5.0 mm in length to aid in fixation. Additionally, curved struts 510a, 510b may apply a small radial force on the surrounding tissue. For example, the applied force may be enough to maintain contact to avoid thrombus, but not enough damage the tissue. In at least some examples, a radial force of between about 0.1 N and about 2.0 N may be exerted by the curved struts on the surrounding tissue. The force applied by curved struts on surrounding tissues may also be selected by adjusting the thickness and/or width of the curved struts. In some examples, curved struts 510a, 510b may have a width that is between about 20% to about 50% of struts 252. In some examples, curved struts 510a, 510b may have a wall thickness that is between about 20% to about 50% of struts 252.

In the example shown, the first end 512a of each curved strut 510a is connected to stent 250 at the top of the first full row of cells 254 adjacent inflow end 210 of prosthetic heart valve 500 and the first end 512a of each curved strut 510b is connected to stent 250 at the bottom of the last full row of cells 254 adjacent outflow end 212 of the prosthetic heart valve. Each curved strut 510a extends from its connection to stent 250 downwardly towards a midsection M of heart valve 500 and radially outwardly from the stent. Likewise, each curved strut 510b extends from its connection to stent 250 upwardly toward midsection M and radially outwardly from the stent. The connection of the curved struts to cells 254 does not have to be at the junction of two struts 252. Rather, as shown in FIG. 5, prosthetic heart valve 500 may include curved struts 510c that are coupled to selected struts 252a, 252b at spaced distances from the junction between the two. In this example, two curved struts 510c originate from one cell 254. This configuration of two curved struts 510c per cell 254 may be termed a "double takeoff" configuration and may be repeated at inflow end 210, outflow end 212, or both the inflow end and the outflow end. This "double takeoff" configuration may also alternate with the single curved struts 510a, 510b, or replace all of the single curved struts 510a, 510b.

Figure 6A:
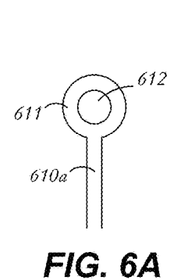
FIGS. 6A-L are schematic representations of several variations of the terminal ends of selected struts.

Each curved strut 510a, 510b, 510c may terminate in a substantially circular eyelet 530 that forms a smooth and blunted shape at its free end 512b to prevent trauma to heart tissue. As shown in greater detail in FIG. 6A, strut 610a may terminate in circular eyelet 611, having an aperture 612. Aperture 612 may be useful to mate with portions of a delivery device for maneuvering and positioning heart valve 500 during deployment. Instead of round eyelets, curved struts 510a, 510b, 510c may have other smoothly curved eyelets on their free ends, such as oval or elliptical eyelets. Further, these smoothly curved structures need not include an aperture, but may be in the form of a solid disk, oval or ellipse. Alternatively, one or more of curved struts 510a, 510b 510c may include an anchoring feature at its free end as will be described with reference to FIGS. 6B-L. In the following examples, reference may be made to anchoring to heart tissue. It is intended by this that the features described may couple to at least one of an atrial wall, a ventricular wall, a native valve leaflet, heart muscle, papillary muscles, tendons, chordae tendineae or any other tissue adjacent a heart valve, such as a mitral valve or a tricuspid valve. Unless otherwise noted, each of the features shown in FIGS. 6A-6L and described below (or described above in the case of the feature of FIG. 6A) may be provided on any one or more of the curved struts of prosthetic heart valve 500.

Figure 6B:
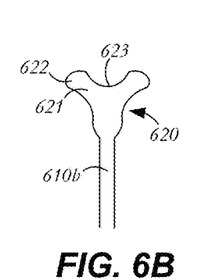
Figure 6C:
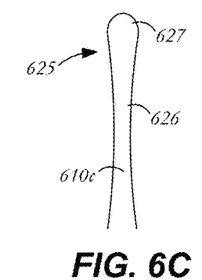
Figure 6D:
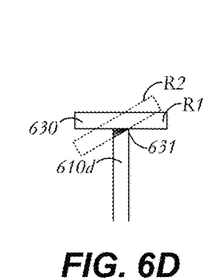
Figure 6E:
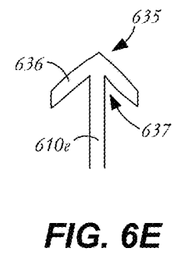
Figure 6F:
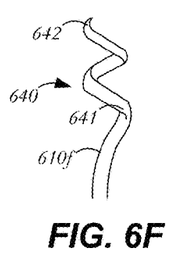
Figure 6G:
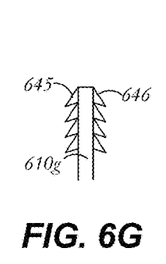
Figure 6H:
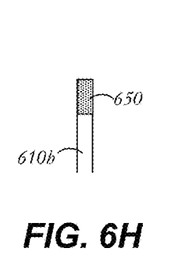
Figure 6I:
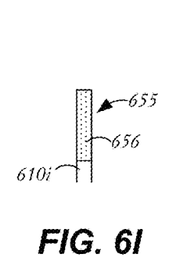
Figure 6J:
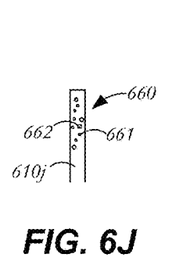
Figure 6K:
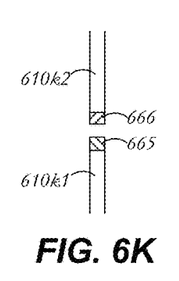
Figure 6L:
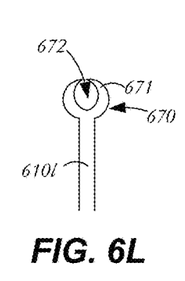

FIG. 6B illustrates a variation in which strut 610b terminates in a bell-shaped end 620 having a broad base 621 composed of two convex ends 622 that are curved and disposed on either side of a middle depressed portion 623. Without being bound to any particular theory, it is believed that broad base 621 provides a larger surface area for pushing against native tissue and reduces the risk of trauma to heart tissue, and that depressed portion 623 may provide a region to which chordae tendineae may attach. FIG. 6C illustrates another variation in which strut 610c terminates in a rounded end 625 having a narrowed neck 626 and a bulbous crown 627. Narrowed neck 626 may add flexibility to strut 610c while bulbous crown 627 provides an atraumatic contact point with body tissue. FIG. 6D illustrates another variation in which strut 610d includes a pivoting head 630 that is capable of rotating at pivot 631 to alternate between a first position R1 and a second position R2 shown in phantom lines at an oblique angle to the strut. It will be understood that pivoting head 630 may be heat set or otherwise shape set so as to be disposed in position R2 during delivery of prosthetic heart valve 500 into the patient, and may then return to position R1 after deployment for anchoring. In FIG. 6E, strut 610e terminates in arrow-shaped end 635 having two outwardly extending wings 636 defining a cavity 637 between strut 610e and each wing. Cavities 637 may capture certain portions of the heart tissue such as, for example, chordae tendineae. FIG. 6F illustrates strut 610f which terminates in corkscrew 640 formed of a helical member 641 that progressively narrows to a point 642. Corkscrew 640 may be configured to engage certain heart tissue by having the tissue wrap around the progressively narrowing member or by piercing the tissue with point 642. A similar configuration, shown in FIG. 6G, illustrates strut 610g having opposing teeth-like barbs 645, 646 which capture heart tissue. Each barb 645, 646 is substantially triangular and angled slightly away from the free end of strut 610g such that the teeth are capable of grasping onto heart tissue when implanted. FIG. 6H illustrates another example for anchoring a strut to heart tissue. Strut 610h includes an energy-excitable region 650, for example, having bio-glues like cyanoacrylates that bonds to heart tissue when excited by an energy source (e.g., laser energy, ultrasound, etc.). Instead of an energy-excitable region, strut 610i of FIG. 6I includes a chemical bonding portion 655, which includes a coating on strut 610i to aid in attachment to heart tissue. In one example, chemical bonding region 655 includes a biocompatible adhesive 656 that is coated onto one or more surfaces of strut 610i. In FIG. 6J, strut 610j includes a region 660 having pores 661. Porous region 660 may be formed from a different material than the remainder of strut 610j and may be biodegradable. Additionally, an adhesive 662 or the like may be added to pores 661 to aid in anchoring. FIG. 6K illustrates two struts 610k1,610k2 each having a polarized region 665,666, respectively. Polarized regions 665,666 may be magnetic and may have opposite polarities such that, when brought close together, struts 610k1,610k2 will be attracted to one another and magnetically clamp onto tissue. In some examples, certain struts that are used for anchoring may be divided into a first group of struts having a first polarized region 610k1 and a second group of struts having a second polarized region 610k2, the first and second polarized regions being of opposite polarities. In at least some examples, struts 610k1 having polarized regions 665 may be in a first row and struts 610k2 having polarized regions 666 may be in a second row, and the two rows may be disposed on opposite sides of heart tissue. In FIG. 6L, strut 610l includes clamp 670 having opposed clamps 671 defining a receiving portion 672 therebetween for receiving a portion of heart tissue.

Figure 7:
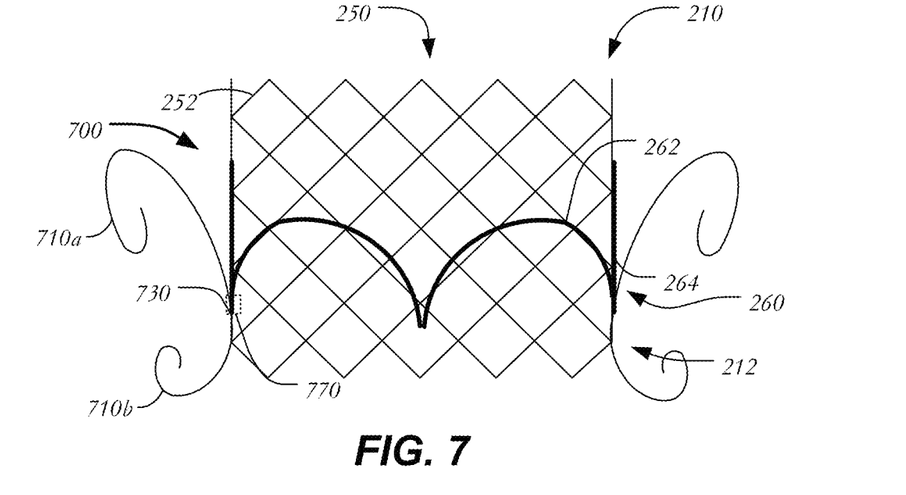
FIG. 7 is a schematic longitudinal cross-section of one embodiment of a prosthetic heart valve having a stent, a valve assembly, and curling struts confined to a region adjacent the outflow section.

FIG. 7 illustrates another variation in which prosthetic heart valve 700 includes projecting curved struts to aid in its fixation to heart tissue. Prosthetic heart valve 700 may extend between inflow end 210 and outflow end 212 and include all the elements described above in connection with heart valve 400, including stent 250 formed of struts 252 defining cells 254, and valve assembly 260 having leaflets 262 and cuff 264. Similar to prosthetic heart valve 400 of FIG. 4, prosthetic heart valve 700 includes upper curling struts 710a and lower curling struts 710b. Curling struts 710a, 710b may be between about 10 mm and about 20 mm. In contrast to prosthetic heart valve 400, however, curling struts 710a-b are arranged in pairs, with each pair originating at a single fixation point 730. In this case, fixation points 730 are disposed close to inflow end 210 (e.g., closer to the atrium when prosthetic heart valve 700 is implanted) to minimize protrusion into the left ventricular outflow tract. In some examples, fixation points 730 may be disposed equidistant between inflow end 210 and outflow end 212. Alternatively, fixation points 730 may be disposed closer to outflow end 212 than to inflow end 210. In at least some examples, curling struts 710a are longer than curling struts 710b and fixation point 730 is disposed closer to outflow end 212 than inflow end 210. Curling struts may apply a radial force on surrounding tissue in the range described above with respect to cured struts. In some examples, curling struts 710a, 710b may have a width that is between about 20% to about 50% of struts 252. In some examples, curling struts 710a, 710b may have a wall thickness that is between about 20% to about 50% of struts 252. Though leaflets 262 and stent 250 are illustrated in a simplified manner, it will be appreciated that leaflets 262 may be attached to stent 250 at commissure features 770 and that fixation points 730 may be disposed adjacent to or at the same longitudinal position as the commissure features as shown, or anywhere between commissure features 770 and outflow end 212.

According to the disclosure, a prosthetic heart valve has an inflow end and an outflow end, and may include a collapsible and expandable stent including a plurality of commissure features, a plurality of first struts and a plurality of second struts, the plurality of first struts defining a substantially cylindrical projection and the plurality of second struts projecting radially outward from the cylindrical portion and configured to couple to adjacent heart tissue to anchor the stent, and a collapsible and expandable valve assembly disposed within the stent and having a plurality of leaflets coupled to the commissure features; and/or the plurality of second struts may include curved struts, the free ends of the curved struts projecting toward a midsection of the stent; and/or the plurality of second struts may include curling struts, the curling struts forming a fiddlehead shape between the first ends and the second ends; and/or the first ends may be disposed adjacent the outflow end; and/or the first ends may be disposed at a longitudinal position between the plurality of commissure features and the outflow end; and/or the free ends may terminate in at least one of a bell-shaped base, a rounded end having a narrowed neck or a bulbous crown; and/or the free ends may terminate in a pivoting head; and/or the free ends may terminate in at least one of an arrow-shaped end, a corkscrew, or a plurality of barbs; and/or the free ends may terminate in at least one of a porous region, a chemical bonding region, or an electrically excitable region; and/or the free ends may terminate in a region coated with a biocompatible adhesive; and/or the free ends of a first group of the second struts may have a first polarity and the free ends of a second group of the second struts may have a second polarity opposite a first polarity; and/or the valve assembly and the stent may be capable of replacing the function of at least one of a native mitral valve and a native tricuspid valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic heart valve having an inflow end and an outflow end, comprising:
    a collapsible and expandable stent including a plurality of commissure features, a plurality of first struts defining a substantially cylindrical portion, a plurality of curled second struts having first ends attached to the cylindrical portion and free ends projecting radially outward from the cylindrical portion to anchor the stent to the heart tissue, the free ends of a first group of the plurality of second struts have a first polarity and the free ends of a second group of the plurality of second struts have a second polarity opposite the first polarity; and
    a collapsible and expandable valve assembly disposed within the stent and having a plurality of leaflets coupled to the commissure features.

2. The prosthetic heart valve of claim 1, wherein the valve assembly and the stent are capable of replacing the function of at least one of a native mitral valve or a native tricuspid valve.

3. The prosthetic heart valve of claim 1, wherein the first ends of the first group of the plurality of second struts are disposed adjacent the outflow end.

4. The prosthetic heart valve of claim 3, wherein the first ends of the second group of the plurality of second struts are disposed adjacent the inflow end.

5. The prosthetic heart valve of claim 4, wherein the free ends of the first group of the plurality of second struts are configured to magnetically clamp to the free ends of the second group of the plurality of second struts on opposite sides of the heart tissue.

* * * * *